US008823802B2

(12) United States Patent
Myrick et al.

(10) Patent No.: US 8,823,802 B2
(45) Date of Patent: Sep. 2, 2014

(54) MULTI-MODE IMAGING IN THE THERMAL INFRARED FOR CHEMICAL CONTRAST ENHANCEMENT

(75) Inventors: Michael Myrick, Irmo, SC (US); Heather Brooke, Alexandria, VA (US); Megan Baranowski, Columbia, SC (US); Jessica McCutcheon, Scranton, SC (US); Stephen Morgan, Columbia, SC (US)

(73) Assignee: University of South Carolina, Columbia, SC (US)

( * ) Notice: Subject to any disclaimer, the term of this patent is extended or adjusted under 35 U.S.C. 154(b) by 1002 days.

(21) Appl. No.: 12/898,024

(22) Filed: Oct. 5, 2010

(65) Prior Publication Data

US 2011/0090342 A1 Apr. 21, 2011

Related U.S. Application Data

(60) Provisional application No. 61/279,106, filed on Oct. 15, 2009.

(51) Int. Cl.
| | |
|---|---|
| *H04N 5/33* | (2006.01) |
| *G01J 3/433* | (2006.01) |
| *G01N 21/88* | (2006.01) |
| *G01N 21/35* | (2014.01) |

(52) U.S. Cl.
CPC . *G01J 3/433* (2013.01); *H05N 5/33* (2013.01); *G01N 21/88* (2013.01); *G01N 21/3563* (2013.01); *G01N 21/35* (2013.01); *G01N 21/3577* (2013.01)
USPC .......................................................... 348/164

(58) Field of Classification Search
CPC .......................................................... H04N 5/33
USPC .......................................................... 348/164
See application file for complete search history.

(56) References Cited

U.S. PATENT DOCUMENTS

| | | |
|---|---|---|
| 5,504,332 A | 4/1996 | Richmond et al. |
| 5,945,676 A | 8/1999 | Khalil et al. |
| 5,946,088 A | 8/1999 | Aldridge |
| 6,260,997 B1 | 7/2001 | Claybourn et al. |
| 6,490,035 B1 | 12/2002 | Folestad et al. |
| 6,504,943 B1 | 1/2003 | Sweatt et al. |
| 6,517,230 B1 | 2/2003 | Afnan et al. |
| 6,776,517 B2 | 8/2004 | Afnan et al. |
| 6,849,460 B2 | 2/2005 | McFarland et al. |
| 7,123,360 B2 | 10/2006 | Treado et al. |
| 7,489,252 B2 | 2/2009 | Long et al. |
| 7,595,734 B2 | 9/2009 | Long et al. |
| 7,623,235 B2 | 11/2009 | Ho et al. |
| 7,623,237 B1 | 11/2009 | Liphardt et al. |
| 7,671,975 B2 | 3/2010 | Mangan et al. |
| 2005/0032235 A1 | 2/2005 | Tummala et al. |
| 2005/0062006 A1 | 3/2005 | Wilfert |

(Continued)

*Primary Examiner* — Geepy Pe
*Assistant Examiner* — James Pontius
(74) *Attorney, Agent, or Firm* — Dority & Manning, P.A.

(57) ABSTRACT

A system and method for analyzing a sample is disclosed. At least a portion of the sample is illuminated with modulated light from a light source, such as an infrared light source. Infrared energy from the sample is monitored with an infrared detector as the sample is being illuminated with the modulated light. The AC response of the infrared energy is analyzed to determine at least one of emission data or reflection data about the sample. The emission data or the reflection data can be used to enhance chemical contrast between varying substances on the sample.

14 Claims, 5 Drawing Sheets

(56) References Cited

U.S. PATENT DOCUMENTS

| | | | |
|---|---|---|---|
| 2007/0021670 A1* | 1/2007 | Mandelis et al. | 600/473 |
| 2007/0201136 A1 | 8/2007 | Myrick et al. | |
| 2008/0276687 A1 | 11/2008 | Myrick et al. | |
| 2009/0073433 A1 | 3/2009 | Myrick et al. | |
| 2009/0140144 A1 | 6/2009 | Myrick et al. | |
| 2009/0216504 A1 | 8/2009 | Priore et al. | |
| 2009/0219512 A1 | 9/2009 | Myrick et al. | |
| 2009/0219538 A1 | 9/2009 | Myrick et al. | |
| 2009/0219539 A1 | 9/2009 | Myrick et al. | |
| 2009/0219597 A1 | 9/2009 | Myrick et al. | |
| 2009/0250613 A1 | 10/2009 | Myrick et al. | |
| 2010/0042348 A1 | 2/2010 | Bakker | |
| 2010/0195105 A1 | 8/2010 | Myrick et al. | |

* cited by examiner

MULTI-MODE IMAGING IN THE THERMAL INFRARED FOR CHEMICAL CONTRAST ENHANCEMENT

PRIORITY CLAIM

This application claims the benefit of priority of U.S. Provisional Patent Application No. 61/279,106, filed Oct. 15, 2009, which is incorporated by reference herein in its entirety for all purposes.

GOVERNMENT SUPPORT CLAUSE

This invention was made with government support under 2007-DN-BX-K199 awarded by the National Institute of Justice (NIJ)/DOJ). The government has certain rights in the invention.

BACKGROUND

The present disclosure relates generally to thermal infrared imaging analysis, and more particularly to multi-mode imaging in the thermal infrared for chemical contrast enhancement.

Non-destructive screening of materials using infrared spectroscopy techniques serves many useful purposes. For instance, in quality control applications, non-destructive screening using infrared spectroscopy techniques can be used to detect the presence of various substances or defects in a sample. In further applications, infrared spectroscopy techniques can be used to detect the presence of blood or other biological fluids during forensic investigations.

Often times it is desirable to provide contrast between various substances. For instance, in forensic investigations, it can be desirable to readily distinguish blood or other biological fluid stains from other substances. In circumstances where substances have overlapping absorbance peaks, chemical contrast detection using infrared spectroscopy can pose many challenges. For instance, traditional infrared measurements of spectrally-overlapped chemical mixtures rely on spectroscopic measurements with multivariate statistics. These traditional methods can be experimentally complicated and can require time and significant expertise in chemometric analysis.

Thus, a need exists for a system and method for multi-mode imaging analysis in the thermal infrared that provides for chemical contrast enhancement where overlapping absorbance peaks are an issue.

SUMMARY

Aspects and advantages of the invention will be set forth in part in the following description, or may be obvious from the description, or may be learned through practice of the invention.

One exemplary embodiment of the present disclosure is directed to a method for analyzing a sample. The method includes illuminating at least a portion of a sample with modulated light from a modulated light source; monitoring infrared energy from the sample using an infrared detector; and analyzing the AC response of the infrared energy to determine at least one of reflection data or emission data about the sample.

In a variation of this exemplary embodiment, the modulated light source can include an infrared light source that can include a chopper or other electrically switched light source.

In another variation of this exemplary embodiment, the infrared detector can include an infrared camera.

In yet another variation of this exemplary embodiment, analyzing the AC response of the infrared energy includes acquiring a plurality of digital infrared images using the infrared detector. Each of the infrared images can include a plurality of pixels. The method can further include analyzing the AC response per pixel of the plurality of digital infrared images to determine at least one of reflection data or emission data about the sample.

In a particular variation of this exemplary embodiment, analyzing the AC response per pixel includes determining an average intensity of each pixel for the plurality of digital infrared images at a given phase relative to the modulated light and plotting the average amplitude of each pixel at the given phase as an AC infrared image. For instance, in a particular embodiment, the given phase relative to the modulated light can be about 0° to provide data analogous to diffuse reflectance of the sample, which can contain significant chemical information. In another embodiment, the given phase relative to the modulated light can be about 90° to provide data analogous to thermal emission of the sample, which can also contain significant chemical information.

In a further variation of this exemplary embodiment, analyzing the AC response per pixel includes determining a first average intensity of each pixel for the plurality of digital infrared images at a first phase, such as at about 0°, relative to the modulated light and plotting the first average intensity of each pixel at the first phase as a first infrared image. The method can further include determining a second average intensity of each pixel for the plurality of digital infrared images at a second phase, such as at about 90°, relative to the modulated light source and plotting the second average intensity of each pixel at the second phase as a second AC infrared image. The method can further include comparing the first AC infrared image and the second AC infrared image to determine chemical contrast between varying substances in the sample.

In yet a further variation of this exemplary embodiment, the method includes comparing the AC response per pixel of the plurality of infrared images to a reference signal synchronous with the modulated light. In still a further variation of this exemplary embodiment, the method can include adjusting the modulation rate of the modulated light.

Another exemplary embodiment of the present disclosure is directed to a thermal imaging system for analyzing a sample. The system includes a light source configured to illuminate at least a portion of a sample with modulated light and an infrared detector configured to monitor infrared energy from the sample. In particular embodiments, the light source can be an infrared light source and can include a chopper or an electrically switched light source. The infrared detector can be an infrared camera. The system further includes a processor configured to analyze the AC response of the infrared energy to determine at least one of reflection data or emission data about the sample.

In a variation of this exemplary embodiment, the infrared detector can be configured to acquire a plurality of digital infrared images of the sample. Each of the plurality of digital infrared images can include a plurality of pixels. The processor can be configured to analyze the AC response per pixel of the plurality of digital infrared images to determine at least one of reflection data or emission data about the sample.

In another variation of this exemplary embodiment, the processor is configured to determine an average intensity for each pixel for the plurality of digital infrared images at a given phase relative to the modulated light. The processor can be further configured to plot the average amplitude of each pixel at the given phase as an AC infrared image on a visual display device. For instance, in a particular embodiment, the given phase relative to the modulated light can be about 0° to provide data analogous to diffuse reflectance of the sample, which can contain significant chemical information. In another embodiment, the given phase relative to the modulated light can be about 90° to provide data analogous to thermal emission of the sample, which can also contain significant chemical information.

In a further variation of this exemplary embodiment, the processor can be configured to determine a first average amplitude of each pixel for the plurality of digital infrared images at a first phase, such as at about 0°, relative to the modulated light. The processor can be further configured to plot the first average amplitude of each pixel as a first AC infrared image on a visual display device. In still a further variation of this exemplary embodiment, the processor can be configured to determine a second average amplitude of each pixel for the plurality of digital infrared images at a second phase, such as at about 90°, relative to the modulated light. The processor can be further configured to plot the first average amplitude of each pixel as a second AC infrared image on a visual display device.

Variations and modifications can be made to these exemplary embodiments of the present disclosure.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
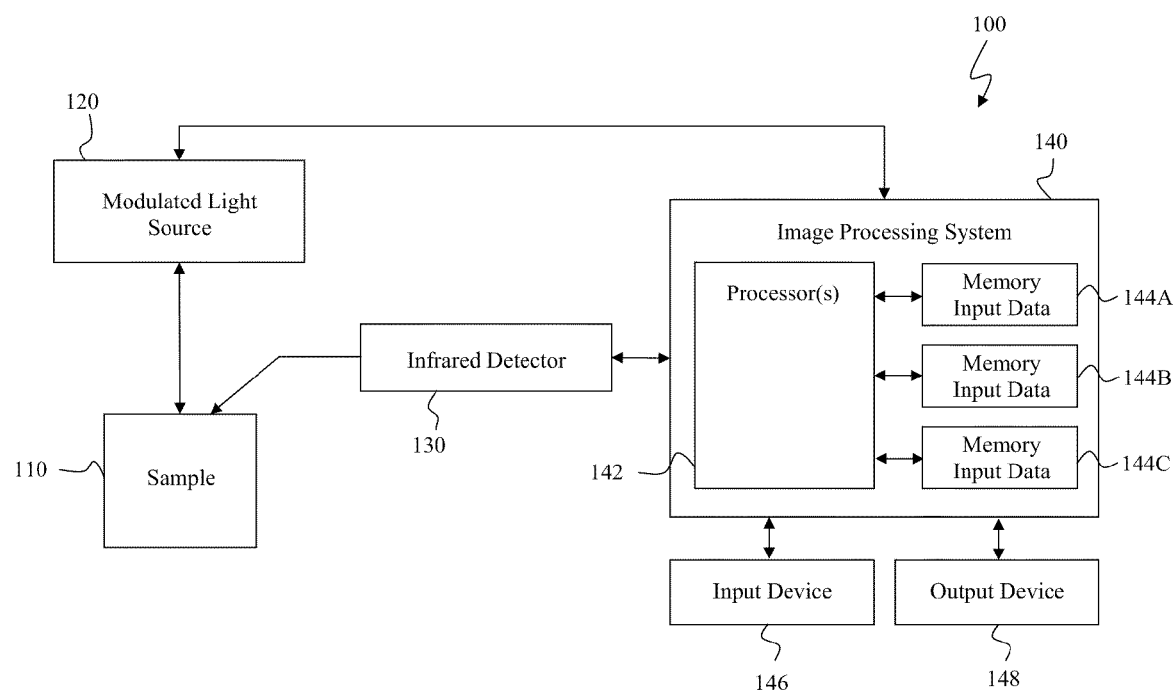
FIG. 1 illustrates a block diagram of an exemplary thermal imaging system according to an exemplary embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present disclosure is directed to thermal imaging of a sample that has been illuminated with a modulated light source. Chemical contrast between various substances in the sample is enhanced by using AC responses as well as lock-in amplifier techniques to acquire reflection data and emission data about the sample.

FIG. 1 illustrates a block diagram of an exemplary thermal imaging system 100 according to an exemplary embodiment of the present disclosure. Thermal imaging system 100 generally includes a modulated light source 120, an infrared detector 130, and an image processing system 140. Image processing system 140 includes various components, including, for instance, a processor(s) 142, various memory elements 144A, 144B, and 144C, as well as an input device 146 and an output device 148.

Thermal imaging system 100 is used to analyze a sample 110. Sample 110 can be any object, item, or product desired to be analyzed. For instance, in particular embodiments, sample 110 can be a product being examined for quality control purposes. In another exemplary embodiment, sample 110 can be an object or item being analyzed for the presence of blood or other biological fluids as part of a forensic investigation. Sample 110 can include various substances with overlapping absorbance peaks. Thermal imaging system 100 can be used to provide enhanced chemical contrast between the varying substances to distinguish varying chemical substances on sample 110.

Light source 120 is used to illuminate at least a portion of a sample 110 with modulated light. In a particular embodiment, light source 120 can be an infrared light source configured to illuminate at least a portion of sample 110 with modulated infrared light. Those of ordinary skill in the art, using the disclosures provided herein, should understand that light source 120 can provide any form of light or energy capable of being absorbed by sample 110 for the detection of heating/cooling effects. The modulated light provided by light source 120 is periodic in nature such that the intensity of the light varies according to a periodic cycle. A chopper or electrically switched light source can be used to provide the modulated light. In other embodiments, a shutter or other optical device can be arranged downstream of light source 120 to modulate the light from light source 120 according to a specific frequency or modulation rate. As will be discussed in more detail below, the modulation rate of the modulated light can be a significant factor in the analysis of the present disclosure, as it can affect the strength of heating/cooling effects.

Infrared detector 130 monitors infrared energy from sample 110 as the sample 110 is being illuminated with modulated light from light source 120. Infrared detector 130 preferably detects light energy being reflected or emitted from sample 110 in the mid-infrared spectrum, such as light energy having a wavelength in the range of about 2.5 μm to about 20 μm. In a particular embodiment, infrared detector 130 includes an infrared camera configured to acquire a plurality of digital infrared images of sample 110 as the sample 110 is being illuminated with modulated light from light source 120. The infrared camera acquires a plurality of digital infrared images (or frames) per cycle of modulated light. For instance, in a particular embodiment, the infrared camera acquires about 30 frames per cycle of modulated light. The speed at which the infrared camera captures digital infrared images can be adjusted based on the modulation rate of the modulated light. In particular embodiments, it is preferred to allow the system to come to steady state before the collection of data by infrared detector 130. This allows for separation of the heating/cooling of sample 110 from overall system changes.

Image processing system 140 is configured to analyze the AC response of the infrared energy detected by infrared detector 130 to determine reflection data or emission data about sample 110. Reflection data and emission data can be used to distinguish varying substances in sample 110 from one another, despite an overlap in absorption peaks for the substances.

The infrared images obtained by infrared detector 130 can be relayed to the image processing system 140, which can include one or more processors 142. Processor(s) 142 can be configured to receive input data including infrared images from infrared detector 130, analyze such infrared images with suitable image analysis techniques, and provide useable output such as data to a user or signals via output device 148.

Various memory/media elements 144 may be provided as a single or multiple portions of one or more varieties of computer-readable media, such as, but not limited to, any combination of volatile memory (e.g., random access memory (RAM, such as DRAM, SRAM, etc.) and nonvolatile memory (e.g., ROM, flash, hard drives, magnetic tapes, CD-ROM, DVD-ROM, etc.) or any other memory devices including diskettes, drives, other magnetic-based storage media, optical storage media and others. Although FIG. 1 shows three separate memory/media elements 144A, 144B, and 144C, the content dedicated to such devices may actually be stored in one memory/media element or in multiple elements. Any such possible variations and other variations of data storage, using the disclosures provided herein, will be appreciated by one of ordinary skill in the art.

The computing/processing devices of FIG. 1 may be adapted to function as a special-purpose machine providing desired functionality by accessing software instructions rendered in a computer-readable form stored in one or more of the memory/media elements (e.g., memory/media element 144B). When software is used, any suitable programming, scripting, or other type of language or combinations of languages may be used to implement the teachings contained herein. In other embodiments, the methods disclosed herein may alternatively be implemented by hard-wired logic or other circuitry, including, but not limited to application-specific circuits.

Other memory/media elements (e.g., memory/media elements 144A, 144B) are used to store data which will also be accessible by the processor(s) 142 and which will be acted on per the software instructions stored in memory/media element 144B. For example, memory/media element 144A can include input data corresponding to infrared images obtained from the infrared detector 130 as well as any predetermined parameters. Such predetermined parameters may be pre-programmed into memory/media element 144A or provided for storage therein when entered as input data from a user accessing the input device 146.

Input device 146 may correspond to one or more peripheral devices configured to operate as a user interface with image processing system 140. Exemplary input devices may include, but are not limited to, a keyboard, touch-screen monitor, microphone, mouse and other suitable input devices.

Second memory element 144B includes computer-executable software instructions that can be read and executed by processor(s) 142 to act on the input data stored in memory/media element 144A to create new output data (e.g., surface anomaly identification, location, and classification) for storage in a third memory/media element 144C. Selected portions of the output data may then be provided to one or more peripheral output devices 148. Output device 148 may correspond to a display such as a monitor, screen, or other visual display, a printer, or the like.

Figure 2:
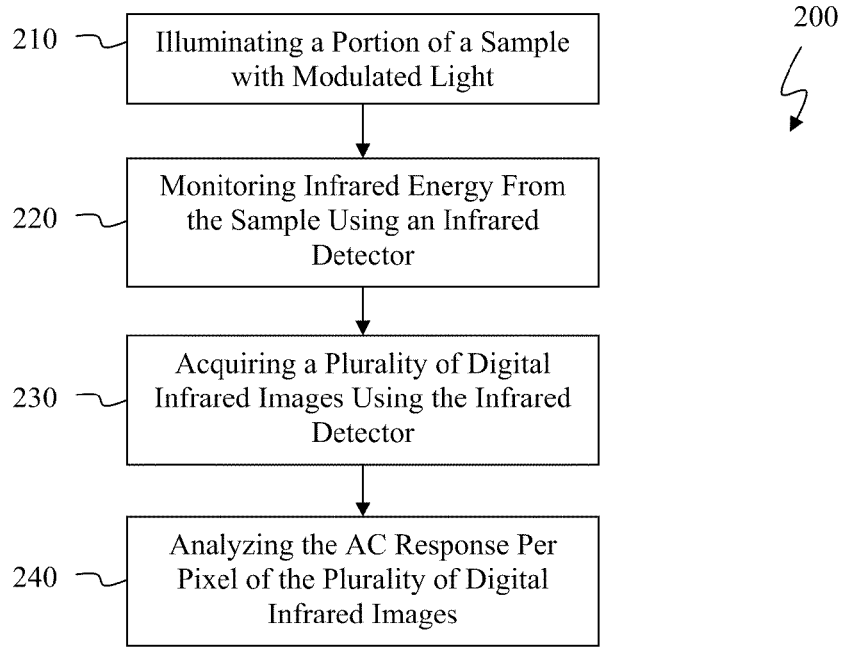
FIG. 2 illustrates a flow chart of exemplary method steps according to an exemplary embodiment of the present disclosure.

With reference now to FIG. 2, exemplary method steps performed by system 100 in accordance with an exemplary embodiment of the present disclosure will now be set forth in detail. At 210, the method 200 includes illuminating a portion of a sample with modulated light from a light source, such as light source 120 of FIG. 1. As discussed above, modulated light can include any light capable of being absorbed by a sample for determination of heating/cooling effects.

At 220, the method 200 includes monitoring infrared energy (either through reflection, emission, or otherwise) from the sample using an infrared detector, such as infrared detector 130 of FIG. 1. At 230, the method 200 includes acquiring a plurality of digital infrared images of the sample using the infrared detector. For instance, in a particular embodiment, an infrared camera acquires a plurality of digital infrared images of the sample as the sample is being illuminated with modulated light. Preferably, the infrared detector can obtain a plurality of digital infrared images per cycle of modulated light.

Figure 4:
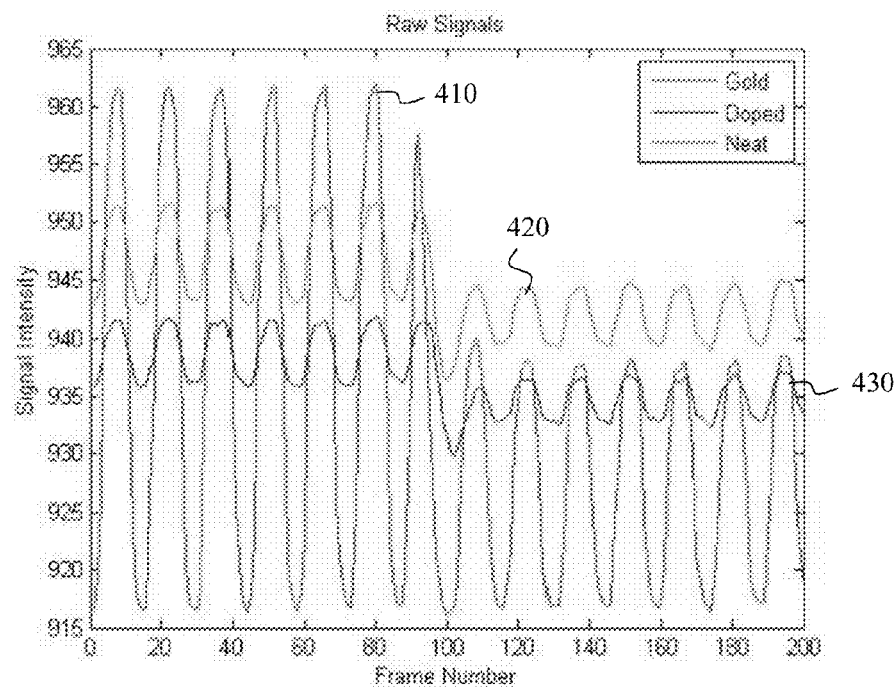
FIG. 4 provides a graphical representation of exemplary pixel AC response curves for neat and doped fabric samples and a gold standard reference according to an exemplary embodiment of the present disclosure.

Finally, at 240, the method 200 includes analyzing the AC response per pixel of the digital infrared images to determine reflection data or emission data about the sample. An exemplary signal response per pixel is illustrated in FIG. 4, which represents the pixel response through a plurality of digital infrared images acquired during a measurement. FIG. 4 provides three curves 410, 420, and 430.

Curve 410 represents the pixel response from a reference signal that is synchronous with the modulated light. For instance, in a particular embodiment, the sample can include a gold standard that is used to recognize the phase of the light source. The gold standard should have a response that is in phase with the modulated light. Those of ordinary skill in the art, using the disclosures provided herein, should understand that a reference signal is not necessary to perform the techniques in accordance with embodiments of the present disclosure, but simplifies the task. A separate signal of any type that is synchronous with the modulated light can be chosen for this purpose.

Curve 420 and curve 430 represent an exemplary pixel response of neat and doped fabric samples respectively. The left hand part of the curve is a response from a raw infrared camera and the right hand part of the curve is a response from an infrared camera with a chemical filter in place.

Figure 5:
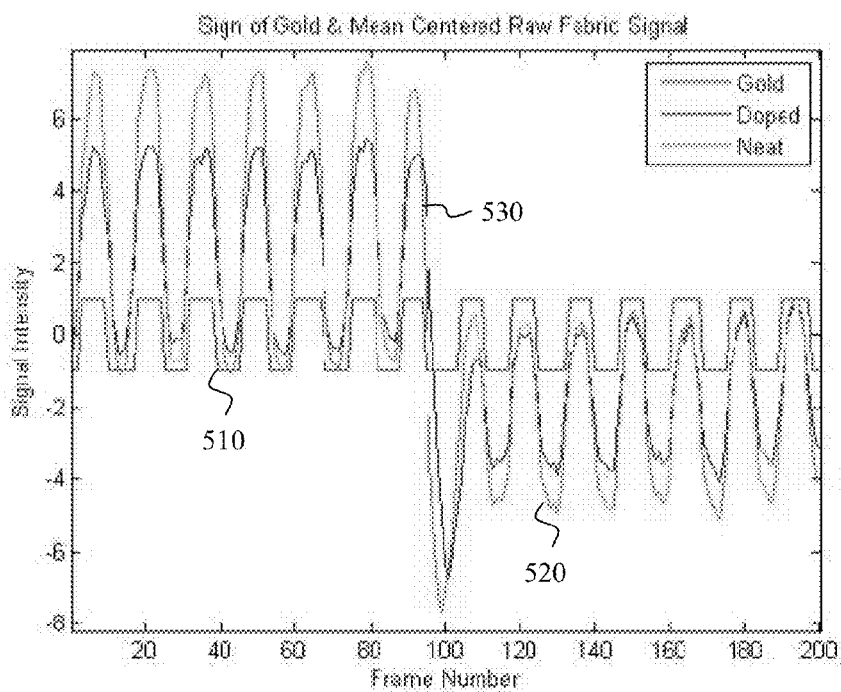
FIG. 5 provides a graphical representation of exemplary pixel AC response curves after averaging for neat and doped fabric samples and a gold standard reference according to an exemplary embodiment of the present disclosure.

FIG. 5 depicts an exemplary signal response per pixel after mean-centering and a reference square wave. Curve 510 represents the reference square wave obtained based on a gold standard. Curves 520 and curve 530 represent an exemplary pixel response to neat and doped fabric samples respectively.

The left hand part of the curve is a response from a raw infrared camera and the right hand part of the curve is a response from an infrared camera with a chemical filter in place.

The AC response per pixel can be analyzed by determining an average intensity for each pixel for the plurality of digital images at a given phase relative to the modulated light. At a given phase relative to the modulated light refers to the phase of modulated light to which a particular digital image corresponds. As discussed above, the infrared detector acquires a plurality of digital images per cycle of modulated light. Each of these digital images can be associated with a particular phase of the modulated light. For instance, the digital image that occurs when the modulated light is at or about the 0° phase is associated with the 0° AC response of the sample. The digital image that occurs when the modulated light is at or about the 90° phase is associated with the 90° response of the sample. The average pixel data for a given phase relative to the modulated light can then be plotted as an AC infrared image. The AC infrared image can include reflection or emission data about the sample.

In a particular embodiment, the signal analysis is analogous to that done by a lock-in amplifier. The analysis is used to determine the average amplitude of oscillation of the intensity of each pixel through the plurality of digital infrared images for a given phase of detection relative to the modulated light. For instance, the average intensity can be determined at about a 0° phase relative to the modulated light or at about a 90° phase relative to the modulated light. All of the data in the truncated array can be mean-centered, multiplied by the in-phase square wave, and then each pixel can be averaged, or summed through the time dimension. The data can then be plotted as an image, with or without some form of normalization.

Figure 3:
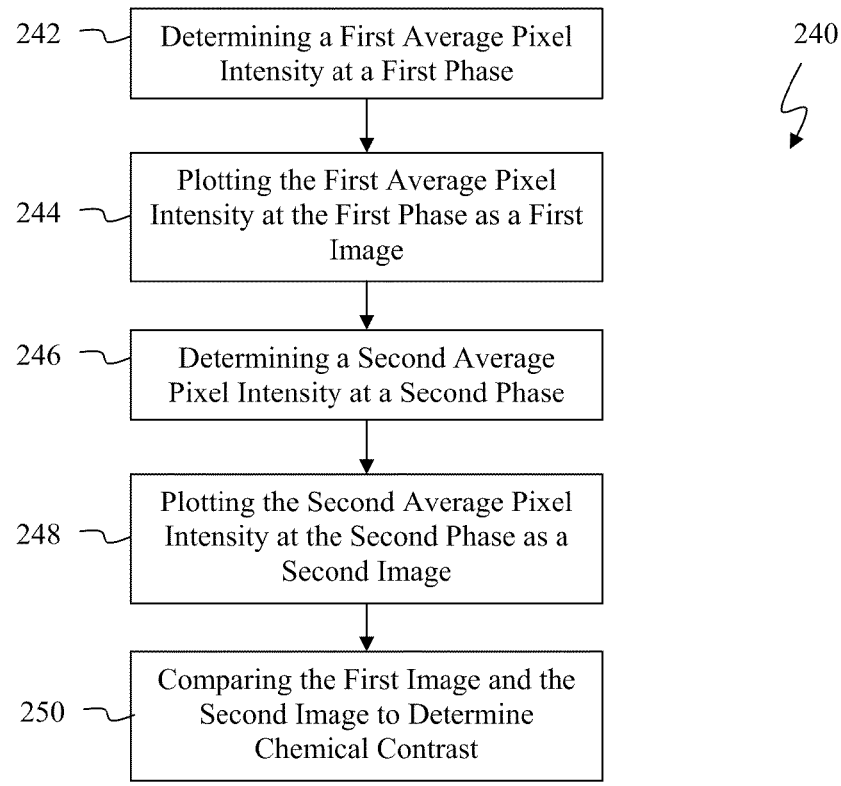
FIG. 3 illustrates a flow chart of exemplary method steps according to an exemplary embodiment of the present disclosure.

By analyzing the AC response of the infrared images, chemical contrast between varying substances on the sample can be enhanced. For instance, referring to FIG. 3, analyzing the AC response per pixel can include at 242 determining a first average pixel intensity at a first phase relative to the modulated light. At 244, the first average pixel intensity at the first phase is plotted as a first AC infrared image. At 246, a second average pixel intensity at a second phase relative to the modulated light is determined. At 248, the second average pixel intensity at the second phase is plotted as a second AC infrared image. At 250, the first AC infrared image and the second AC infrared image can be compared to determine chemical contrast between varying substances on the sample.

For instance, in a particular embodiment, an average pixel intensity at a 0° phase is determined and plotted as a 0° AC infrared image. The 0° phase AC infrared image can include information analogous to the diffuse reflectance of the sample, which contains significant chemical information. The average pixel intensity at a 90° phase can then be determined and plotted as a 90° AC infrared image. The 90° phase AC infrared image includes information concerning the thermal emission of the sample. The 90° phase AC infrared image is orthogonal to the reflectance measurement, and can also contain chemically sensitive information.

The modulation rate of the modulated light is significant factor in generating the 90° AC infrared image because high modulation rates lead to low modulation of emission. Moreover, there is a trade off between excitation brightness and the modulation rate. In particular, a high intensity source would lend itself to a higher modulation rate. Thus, the modulation rate of the modulated light can be adjusted to achieve optimum or more desired 90° phase AC infrared image measurements.

As illustrated in the following example, chemical contrast between varying chemical substances on the sample can be determined by comparing the 0° AC infrared image and the 90° AC infrared image.

EXAMPLE

Figure 6:
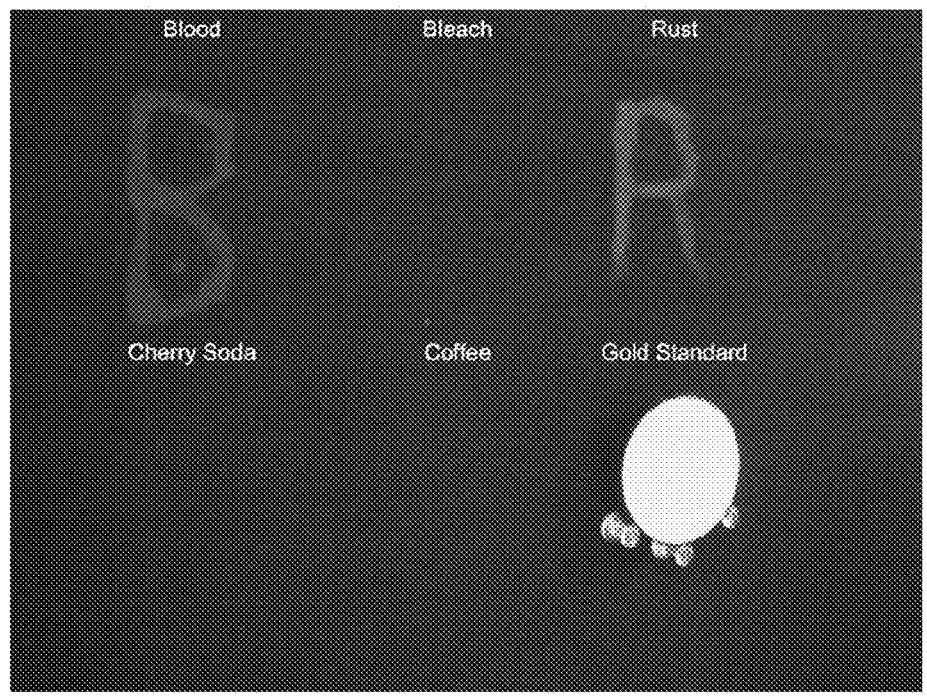
FIG. 6 illustrates an exemplary sample with various stains including a blood stain.

FIG. 6 depicts an exemplary sample of acrylic with five different types of stains that have been pipetted onto it. The stains were allowed to dry overnight before any data was collected. From the left to right the stains are: whole rat blood, bleach, rust, cherry soda, and coffee. A gold standard was placed in the bottom right corner to allow for normalization of the image. The analyte that was being detected for is the blood. The other materials were chosen because they sometimes give false positives to either or both the Luminol or benzidine detection methods for blood.

Figure 7:
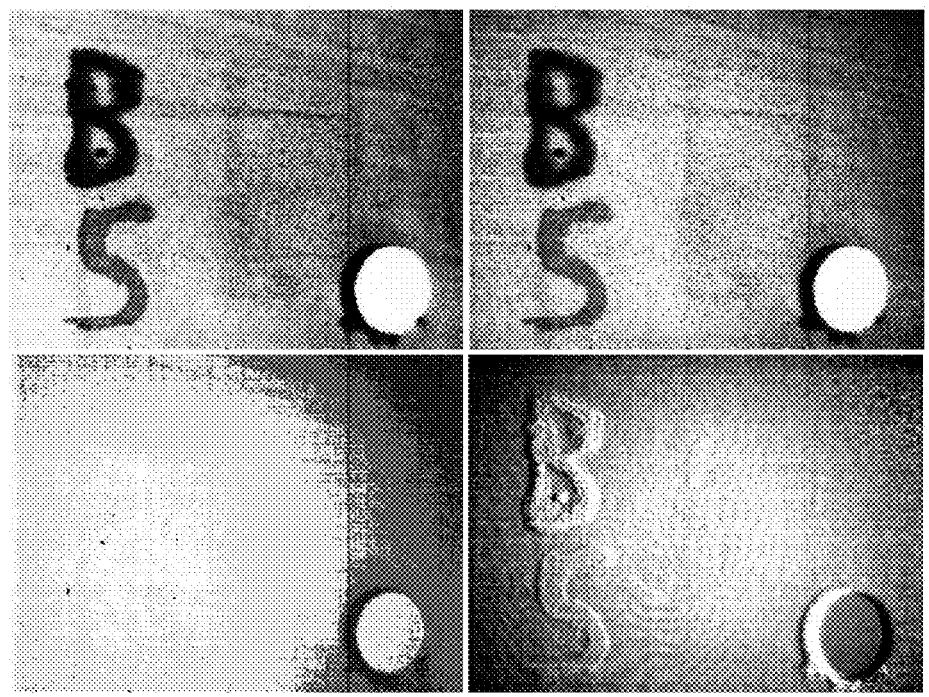
FIG. 7 illustrates an AC infrared image of the exemplary sample of FIG. 6 generated according to an exemplary embodiment of the present disclosure using average intensity of each pixel at about a 0° phase relative to modulated light.

FIG. 7 depicts an AC infrared image generated according to embodiments of the present disclosure at a 0° phase relative to the modulated light. The AC infrared image of FIG. 7 includes diffuse reflectance information for the sample. The image shown is from the data collected while a filter of Albumin (~18 μm) was in place. This shows that by determining diffuse reflectance characteristics of the sample and through use of the Albumin filter, there is discrimination between blood and bleach, rust and coffee. There is not discrimination between blood and soda by this image alone.

Figure 8:
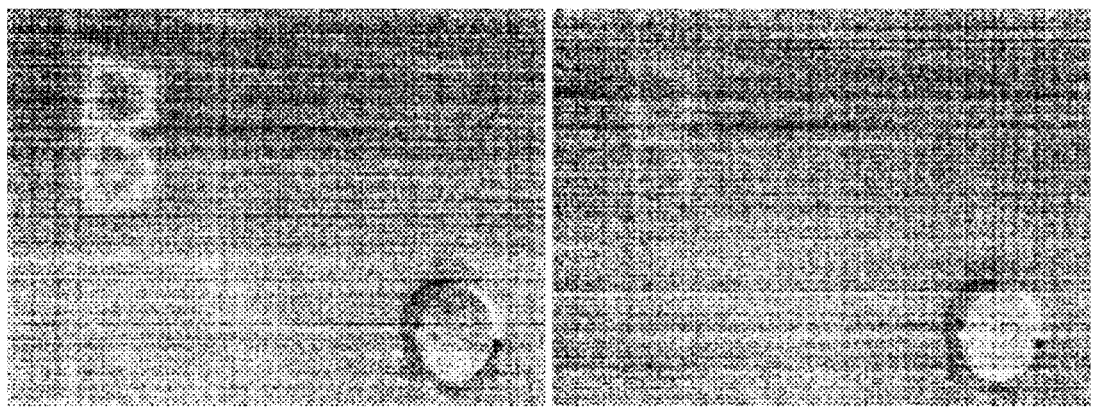
FIG. 8 illustrates an AC infrared image of the exemplary sample of FIG. 6 generated according to an exemplary embodiment of the present disclosure using an average intensity of each pixel at about a 90° phase relative to modulated light.

FIG. 8 depicts an AC infrared image generated according to embodiments of the present disclosure at a 90° phase relative to the modulated light. The AC infrared image of FIG. 8 includes emission information for the sample. In this image, only the blood stain is visible. These data illustrate that the techniques according to embodiments of the present disclosure can be a viable non-destructive chemical detection technique. One skilled in the art, using the disclosures provided herein, will recognize that this technique is not limited to blood or proteins, but would include any substance that has a unique spectral profile.

In addition, U.S. Patent Application Publication No. 2009/0250613, which is incorporated by reference herein for all purposes, discloses the use of chemical filters to classify particular chemicals using infrared reflectance imaging. It will be clear to one skilled in the art that this method can also be employed with both reflectance and emission imaging in accordance with embodiments of the present disclosure. One of ordinary skill in the art, using the disclosures provided herein, will also understand that any wavelength of light that can be absorbed can lead to 90° phase thermal imaging. It will also be clear that phase shifts other than 0° or 90° could be optimal depending on the temporal shape of reflectance or heating pulses.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for analyzing a sample, comprising:
   illuminating at least a portion of a sample with modulated light from a modulated light source;

monitoring infrared energy from the sample using an infrared detector; and analyzing the AC response of the infrared energy to determine at least one of reflection data or emission data about the sample wherein analyzing the AC response of the infrared energy comprises:

accessing a first AC image of the sample associated with a first phase relative to the modulated light, the first AC image associated with an AC response per pixel for one or more digital images captured when the modulated light is at the first phase;

accessing a second AC image of the sample associated with a second phase relative to the modulated light, the second AC image associated with an AC response per pixel for one or more digital images captured when the modulated light is at the second phase, further wherein the first AC image and the second AC infrared image depict the same sample; and comparing the first AC image with the second AC image to determine chemical contrast between varying substances in the sample.

2. The method of claim 1, wherein die modulated light source comprises an infrared light source.

3. The method of claim 1, wherein analyzing the AC response of the infrared energy comprises:

acquiring a plurality of digital infrared images using the infrared detector, each of the plurality of digital infrared images comprising a plurality of pixels; and analyzing the AC response per pixel of the plurality of digital infrared images to determine at least one of reflection data or emission data about the sample.

4. The method of claim 3, wherein analyzing the AC response per pixel comprises:

determining an average intensity of each pixel for the plurality of digital infrared images at a given phase relative to the modulated light; and plotting the average amplitude of each pixel at the given phase as an AC infrared image.

5. The method of claim 4, wherein the given phase relative to the modulated light is 0°.

6. The method of claim 4, wherein the given phase relative to the modulated light is 90°.

7. The method of claim 1, wherein the method comprises adjusting the modulation rate of the modulated light.

8. The method of claim 1, wherein the infrared detector comprises an infrared camera.

9. A thermal imaging system for analyzing a sample, comprising:

a light source configured to illuminate at least a portion of a sample with modulated light;

an infrared detector configured to monitor infrared energy from the sample;

a processor configured to analyze the AC response of the infrared energy to determine at least one of reflection data or emission data about the sample wherein said processor is configured to display a first AC image of the sample associated with a first phase relative to the modulated light on a visual display device, the first AC image associated with an AC response per pixel for one or more digital images captured when the modulated light is at the first phase; said processor further configured to display a second AC image of the sample associated with a second phase relative to the modulated light on a visual display device, the second AC image associated with an AC response per pixel for one or more digital images captured when the modulated light is at the second phase, further wherein the first AC image and the second AC infrared image depict the same sample;

whereby the first AC image can be compared with the second AC image to determine chemical contrast between varying substances in the sample.

10. The thermal imaging system of claim 9, wherein said modulated light source comprises an infrared light source.

11. The thermal imaging system of claim 9, wherein said modulated light source comprises a chopper or an electrically switched light source.

12. The thermal imaging system of claim 9, wherein said infrared detector comprises an infrared camera.

13. The thermal imaging system of claim 9, wherein the first phase relative to the modulated light is 0°.

14. The thermal imaging system of claim 9, wherein the second phase relative to the modulated light is 90°.

* * * * *

UNITED STATES PATENT AND TRADEMARK OFFICE
CERTIFICATE OF CORRECTION

PATENT NO. : 8,823,802 B2
APPLICATION NO. : 12/898024
DATED : September 2, 2014
INVENTOR(S) : Myrick et al.

It is certified that error appears in the above-identified patent and that said Letters Patent is hereby corrected as shown below:

In The Claims

Column 9, Line 23 "...wherein die modulated..." should read --...wherein the modulated...--

Signed and Sealed this
Ninth Day of June, 2015

Michelle K. Lee
*Director of the United States Patent and Trademark Office*